US011481944B2

(12) United States Patent
Usuda

(10) Patent No.: US 11,481,944 B2
(45) Date of Patent: Oct. 25, 2022

(54) MEDICAL IMAGE PROCESSING APPARATUS, MEDICAL IMAGE PROCESSING METHOD, PROGRAM, AND DIAGNOSIS SUPPORT APPARATUS

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/230,024

(22) Filed: Apr. 14, 2021

(65) Prior Publication Data

US 2021/0233298 A1 Jul. 29, 2021

Related U.S. Application Data

(63) Continuation of application No. PCT/JP2019/042160, filed on Oct. 28, 2019.

(30) Foreign Application Priority Data

Nov. 1, 2018 (JP) .............................. JP2018-206759

(51) Int. Cl.
*G06T 11/60* (2006.01)
*A61B 1/00* (2006.01)
(52) U.S. Cl.
CPC ............ *G06T 11/60* (2013.01); *A61B 1/0005* (2013.01)
(58) Field of Classification Search
CPC ...................................................... G06T 11/60
See application file for complete search history.

(56) References Cited

U.S. PATENT DOCUMENTS

2009/0202179 A1   8/2009   Shivanna et al.
2012/0220840 A1   8/2012   Morita et al.
(Continued)

FOREIGN PATENT DOCUMENTS

JP   2013-000403 A   1/2013
WO   2016/199273 A1   12/2016
(Continued)

OTHER PUBLICATIONS

The extended European search report issued by the European Patent Office dated Sep. 21, 2021, which corresponds to European Patent Application No. 19879182.4-1122 and is related to U.S. Appl. No. 17/230,024.

(Continued)

*Primary Examiner* — Shivang I Patel
(74) *Attorney, Agent, or Firm* — Studebaker & Brackett PC

(57) ABSTRACT

Provided are a medical image processing apparatus, a medical image processing method, a program, and a diagnosis support apparatus that report a region of interest without hindering observation of the boundary between the region of interest and a region of non-interest in a medical image. A medical image processing apparatus includes a superimposition processing unit that superimposes, on a medical image, a figure for reporting a region of interest included in the medical image. The superimposition processing unit superimposes the figure on an inside of the region of interest such that at least part of a boundary between the region of interest and a region of non-interest is not superimposed with the figure, thereby reporting the region of interest without hindering observation of the boundary between the region of interest and the region of non-interest.

14 Claims, 15 Drawing Sheets

(56) References Cited

U.S. PATENT DOCUMENTS

| | | | |
|---|---|---|---|
| 2018/0098690 A1 | 4/2018 | Iwaki | |
| 2018/0242817 A1 | 8/2018 | Imaizumi et al. | |
| 2018/0307933 A1* | 10/2018 | Iwaki | A61B 1/04 |
| 2019/0015163 A1* | 1/2019 | Abhari | G06T 11/60 |

FOREIGN PATENT DOCUMENTS

| | | |
|---|---|---|
| WO | 2017/073338 A1 | 5/2017 |
| WO | 2017/115442 A1 | 7/2017 |

OTHER PUBLICATIONS

International Search Report issued in PCT/JP2019/042160; dated Dec. 10, 2019.

International Preliminary Report on Patentability and Written Opinion issued in PCT/JP2019/042160; dated Apr. 27, 2021.

An Office Action; "Notice of Reasons for Refusal", mailed by the Japanese Patent Office dated Mar. 1, 2022, which corresponds to Japanese Patent Application No. 2020-553888 and is related to U.S. Appl. No. 17/230,024; with English language translation.

* cited by examiner

MEDICAL IMAGE PROCESSING APPARATUS, MEDICAL IMAGE PROCESSING METHOD, PROGRAM, AND DIAGNOSIS SUPPORT APPARATUS

CROSS-REFERENCE TO RELATED APPLICATIONS

The present application is a Continuation of PCT International Application No. PCT/JP2019/042160 filed on Oct. 28, 2019 claiming priority under 35 U.S.C § 119(a) to Japanese Patent Application No. 2018-206759 filed on Nov. 1, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing method, a program, and a diagnosis support apparatus, and specifically relates to a technique of reporting a region of interest in a medical image.

2. Description of the Related Art

There has been known a technique of detecting a region of interest, such as a lesion, from a medical image, and displaying a bounding box (a rectangle surrounding the region) or the like to report that the region of interest has been detected to a medical doctor.

WO2017/073338A describes that, in a case where a lesion is detected from an image during endoscopy, a lesion region in the image displayed on a monitor is surrounded with a frame to report the lesion. WO2017/115442A describes a method of displaying information indicating a lesion position at a place other than an observation image displayed on a monitor.

SUMMARY OF THE INVENTION

To cause a medical doctor to recognize a lesion position without moving his/her line of sight, it is necessary to display a lesion region on a monitor on which the medical doctor is observing an image. On the other hand, when the medical doctor visually compares the lesion region with a normal mucous membrane around the lesion region, the contrast at the boundary of the lesion region is used as a basis for judgement, and thus it is necessary to display the lesion region such that observation of the boundary of the lesion region is not hindered as much as possible.

If a figure surrounding a lesion region is displayed as described in WO2017/073338A, there is a risk that the boundary of the region lesion is difficult to be visually recognized. If a figure surrounding the lesion region is displayed such that the figure does not overlap the boundary of the lesion region, the figure significantly extends off the lesion region, and there is a risk that observation of a normal mucous membrane is hindered, which may lead to oversight of a lesion.

The present invention has been made in view of these circumstances, and an object of the present invention is to provide a medical image processing apparatus, a medical image processing method, a program, and a diagnosis support apparatus that report a region of interest without hindering observation of the boundary between the region of interest and a region of non-interest in a medical image.

To achieve the above-described object, an aspect of a medical image processing apparatus is a medical image processing apparatus including a superimposition processing unit that superimposes, on a medical image, a figure for reporting a region of interest included in the medical image. The superimposition processing unit superimposes the figure on an inside of the region of interest such that at least part of a boundary between the region of interest and a region of non-interest is not superimposed with the figure.

According to this aspect, the figure is superimposed on the region of interest included in the medical image such that at least part of the boundary between the region of interest and the region of non-interest is not superimposed with the figure. Thus, it is possible to report the region of interest without hindering observation of the boundary between the region of interest and the region of non-interest in the medical image.

Preferably, the medical image processing apparatus includes an image acquiring unit that acquires the medical image, and a region-of-interest information acquiring unit that acquires region-of-interest information from the medical image. Accordingly, it is possible to appropriately acquire a medical image and appropriately acquire region-of-interest information.

Preferably, the superimposition processing unit superimposes a figure pointing to the boundary on the region of interest. Accordingly, it is possible to cause a user to recognize the boundary between the region of interest and the region of non-interest.

Preferably, the superimposition processing unit superimposes a figure representing a center of gravity of the region of interest on the region of interest. Accordingly, it is possible to report the region of interest to a user.

Preferably, the superimposition processing unit superimposes the figure, the figure having a size corresponding to an area of the region of interest. Accordingly, it is possible to report the region of interest without hindering observation of the boundary between the region of interest and the region of non-interest in the medical image regardless of the area of the region of interest.

Preferably, the superimposition processing unit superimposes the figure, the figure having a fixed first size, in a case where the area of the region of interest is larger than or equal to a first area. Accordingly, even in a case where the area of the region of interest is larger than or equal to the first area, it is possible to report the region of interest without hindering observation of the boundary between the region of interest and the region of non-interest in the medical image.

Preferably, the superimposition processing unit superimposes the figure, the figure having a fixed second size, in a case where the area of the region of interest is smaller than or equal to a second area. Accordingly, even in a case where the area of the region of interest is smaller than or equal to the second area, it is possible to report the region of interest without hindering observation of the boundary between the region of interest and the region of non-interest in the medical image.

Preferably, the superimposition processing unit superimposes the figure, the figure having a shape corresponding to an area of the region of interest. Accordingly, it is possible to report the region of interest without hindering observation of the boundary between the region of interest and the region of non-interest in the medical image regardless of the area of the region of interest.

Preferably, the superimposition processing unit superimposes a figure pointing to the boundary from the inside of the region of interest in a case where the area of the region of interest is larger than or equal to a third area, and superimposes a figure representing coordinates in the inside of the region of interest in a case where the area of the region of interest is smaller than the third area. Accordingly, even in a case where the area of the region of interest is smaller than the third area, it is possible to report the region of interest without hindering observation of the boundary between the region of interest and the region of non-interest in the medical image.

Preferably, the superimposition processing unit superimposes a figure pointing to the boundary from the inside of the region of interest in a case where the area of the region of interest is larger than or equal to a fourth area, and superimposes the figure on an outside of the region of interest in a case where the area of the region of interest is smaller than the fourth area. Accordingly, even in a case where the area of the region of interest is smaller than the fourth area, it is possible to report the region of interest without hindering observation of the boundary between the region of interest and the region of non-interest in the medical image.

Preferably, the medical image processing apparatus includes a figure generating unit that generates the figure. Accordingly, it is possible to generate a figure to be superimposed on a region of interest.

Preferably, the medical image processing apparatus includes a display control unit that causes a display unit to display the medical image on which the figure is superimposed. Accordingly, a user is able to visually recognize, on the display unit, the medical image on which the figure is superimposed.

To achieve the above-described object, an aspect of a diagnosis support apparatus is a diagnosis support apparatus including the above-described medical image processing apparatus and the display unit.

According to this aspect, the figure is superimposed on the region of interest included in the medical image such that at least part of the boundary between the region of interest and the region of non-interest is not superimposed with the figure. Thus, it is possible to report the region of interest without hindering observation of the boundary between the region of interest and the region of non-interest in the medical image.

To achieve the above-described object, an aspect of a medical image processing method is a medical image processing method including a superimposition processing step of superimposing, on a medical image, a figure for reporting a region of interest included in the medical image. The superimposition processing step superimposes the figure on an inside of the region of interest such that at least part of a boundary between the region of interest and a region of non-interest is not superimposed with the figure.

According to this aspect, the figure is superimposed on the region of interest included in the medical image such that at least part of the boundary between the region of interest and the region of non-interest is not superimposed with the figure. Thus, it is possible to report the region of interest without hindering observation of the boundary between the region of interest and the region of non-interest in the medical image. A program for causing a computer to execute the above-described medical image processing method is also included in this aspect.

According to the present invention, it is possible to report a region of interest without hindering observation of the boundary between the region of interest and a region of non-interest in a medical image.

DESCRIPTION OF THE PREFERRED EMBODIMENTS

Hereinafter, preferred embodiments of the present invention will be described in detail with reference to the attached drawings.

Overall Configuration of Endoscope System

Figure 1:
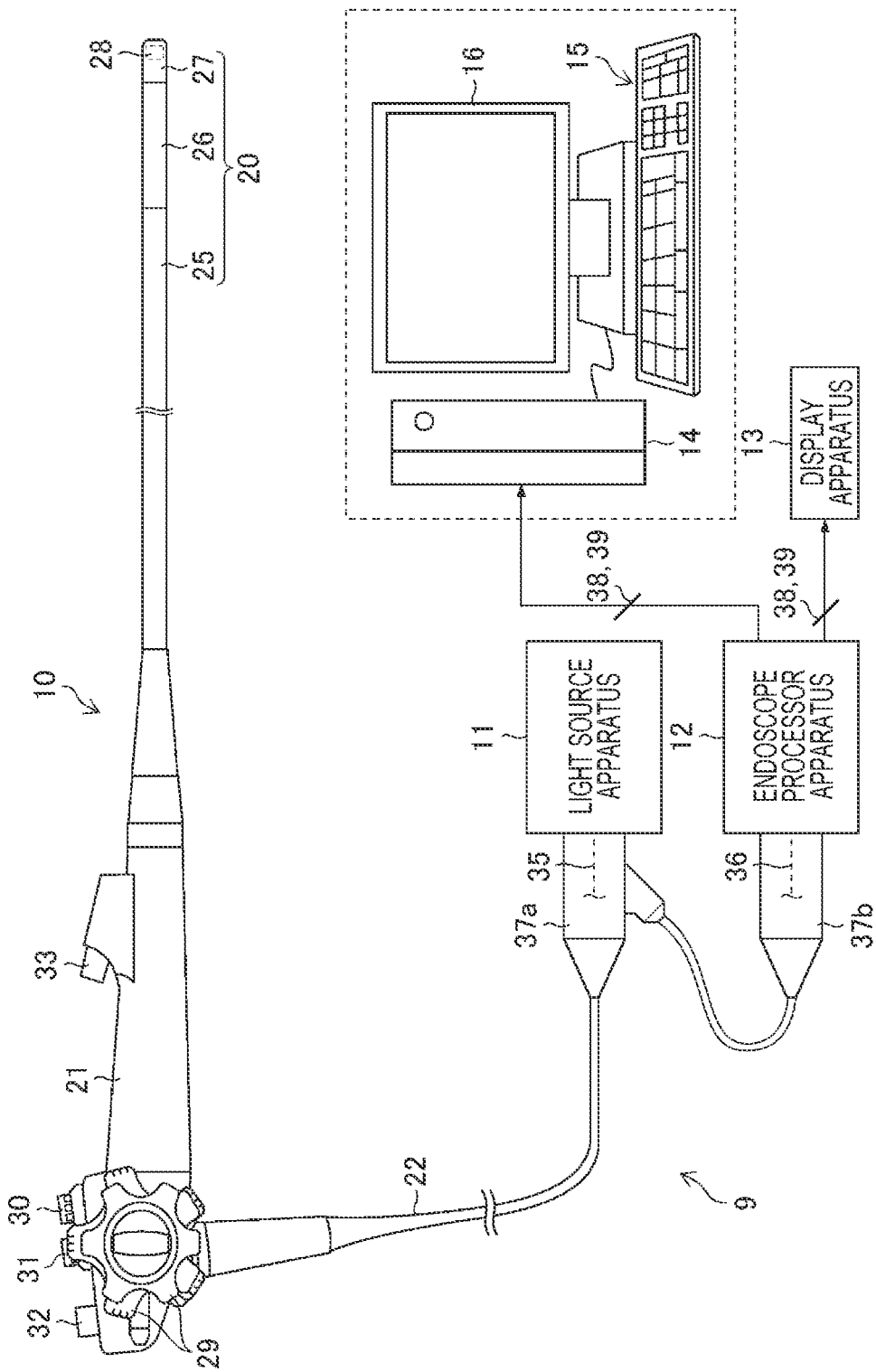
FIG. 1 a schematic diagram illustrating an overall configuration of an endoscope system including a medical image processing apparatus.

FIG. 1 is a schematic diagram illustrating an overall configuration of an endoscope system 9 including a medical image processing apparatus according to the present embodiment. As illustrated in FIG. 1, the endoscope system 9 includes an endoscope 10 which is an electronic endoscope, a light source apparatus 11, an endoscope processor apparatus 12, a display apparatus 13, a medical image processing apparatus 14, an operation unit 15, and a display 16.

The endoscope 10 is for capturing a time-series medical image and is, for example, a soft endoscope. The endoscope 10 has an insertion section 20 that is to be inserted into a subject and that has a distal end and a base end, a handheld operation section 21 that communicates with the base end side of the insertion section 20 and that is to be gripped by a user (medical doctor) to perform various operations, and a universal cord 22 that communicates with the handheld operation section 21.

The insertion section 20 has a small diameter and is elongated as a whole. The insertion section 20 is constituted by a soft part 25 having flexibility, a bending part 26 that can be bent by operating the handheld operation section 21, and a distal end part 27 including therein an imaging optical system (objective lens) that is not illustrated, an imaging device 28, and so forth, which are arranged in this order from the base end side toward the distal end side and communicate with each other.

The imaging device 28 is a complementary metal-oxide semiconductor (CMOS) imaging device or a charge-coupled device (CCD) imaging device. On an imaging surface of the imaging device 28, image light of a portion to be observed is incident through an observation window that is open in a distal end surface of the distal end part 27 and that is not illustrated, and an objective lens that is disposed behind the observation window and that is not illustrated. The imaging device 28 captures the image light of the portion to be observed that has been incident on the imaging surface (converts the image light into an electric signal) and outputs an image signal.

The handheld operation section 21 is provided with various operation members that are to be operated by a user. Specifically, the handheld operation section 21 is provided with two types of bending operation knobs 29 that are to be used in bending operations of the bending part 26, an air/water supply button 30 for an air/water supply operation, and a suction button 31 for a suction operation. The handheld operation section 21 is further provided with a still image capturing instruction unit 32 for providing an instruction to capture a still image 39 of a portion to be observed, and a treatment tool port 33 from which a treatment tool (not illustrated) is to be inserted into a treatment tool insertion path (not illustrated) extending in and through the insertion section 20.

The universal cord 22 is a connection cord for connecting the endoscope 10 to the light source apparatus 11. The universal cord 22 includes therein a light guide 35, a signal cable 36, and a fluid tube (not illustrated) that extend in and through the insertion section 20. In addition, the universal cord 22 has an end portion provided with a connector 37a that is connected to the light source apparatus 11 and a connector 37b that branches off from the connector 37a and that is connected to the endoscope processor apparatus 12.

Connecting of the connector 37a to the light source apparatus 11 causes the light guide 35 and the fluid tube (not illustrated) to be inserted into the light source apparatus 11. Accordingly, necessary illumination light, air, and water are supplied from the light source apparatus 11 to the endoscope 10 through the light guide 35 and the fluid tube (not illustrated). As a result, the illumination light is radiated from an illumination window (not illustrated) on the distal end surface of the distal end part 27 toward a portion to be observed. An operation of pressing the above-described air/water supply button 30 causes air or water to be ejected from an air/water supply nozzle (not illustrated) on the distal end surface of the distal end part 27 toward the observation window (not illustrated) on the distal end surface.

Connecting of the connector 37b to the endoscope processor apparatus 12 causes the signal cable 36 and the endoscope processor apparatus 12 to be electrically connected to each other. Accordingly, an image signal of a portion to be observed is output from the imaging device 28 of the endoscope 10 to the endoscope processor apparatus 12, and a control signal is output from the endoscope processor apparatus 12 to the endoscope 10, through the signal cable 36.

The light source apparatus 11 supplies illumination light to the light guide 35 of the endoscope 10 via the connector 37a. As the illumination light, light in various wavelength ranges is selected in accordance with an observation purpose, for example, white light (light in a white wavelength range or light in a plurality of wavelength ranges), light in one or a plurality of specific wavelength ranges, or a combination thereof. A specific wavelength range is narrower than the white wavelength range.

A first example of the specific wavelength range is, for example, a blue range or green range in a visible range. The wavelength range in the first example includes a wavelength range of 390 nm or more and 450 nm or less or a wavelength range of 530 nm or more and 550 nm or less, and the light in the first example has a peak wavelength in the wavelength range of 390 nm or more and 450 nm or less or the wavelength range of 530 nm or more and 550 nm or less.

A second example of the specific wavelength range is, for example, a red range in the visible range. The wavelength range in the second example includes a wavelength range of 585 nm or more and 615 nm or less or a wavelength range of 610 nm or more and 730 nm or less, and the light in the second example has a peak wavelength in the wavelength range of 585 nm or more and 615 nm or less or the wavelength range of 610 nm or more and 730 nm or less.

A third example of the specific wavelength range includes a wavelength range in which a light absorption coefficient is different between oxyhemoglobin and deoxyhemoglobin, and the light in the third example has a peak wavelength in the wavelength range in which the light absorption coefficient is different between oxyhemoglobin and deoxyhemoglobin. The wavelength range in the third example includes a wavelength range of 400±10 nm, a wavelength range of 440±10 nm, a wavelength range of 470±10 nm, or a wavelength range of 600 nm or more and 750 nm or less, and the light in the third example has a peak wavelength in the wavelength range of 400±10 nm, the wavelength range of 440±10 nm, the wavelength range of 470±10 nm, or the wavelength range of 600 nm or more and 750 nm or less.

A fourth example of the specific wavelength range is a wavelength range (390 nm to 470 nm) of excitation light that is to be used in observation of fluorescence generated by a fluorescent substance in a living body (fluorescence observation) and that excites the fluorescent substance.

A fifth example of the specific wavelength range is a wavelength range of infrared light. The wavelength range in the fifth example includes a wavelength range of 790 nm or more and 820 nm or less or a wavelength range of 905 nm or more and 970 nm or less, and the light in the fifth example has a peak wavelength in the wavelength range of 790 nm or more and 820 nm or less or the wavelength range of 905 nm or more and 970 nm or less.

The endoscope processor apparatus 12 controls operations of the endoscope 10 via the connector 37b and the signal cable 36. The endoscope processor apparatus 12 generates a moving image 38, which is a time-series medical image made up of time-series frame images 38a (see FIG. 2) on the basis of image signals acquired from the imaging device 28 of the endoscope 10 via the connector 37b and the signal cable 36. The moving image 38 has a frame rate of, for example, 30 frames per second (fps).

Furthermore, when the still image capturing instruction unit 32 is operated in the handheld operation section 21 of the endoscope 10, the endoscope processor apparatus 12 acquires, while generating the moving image 38, one frame image 38a in the moving image 38 at the timing of an image capturing instruction and regards the frame image 38a as the still image 39.

The moving image 38 and the still image 39 are each a medical image acquired through imaging of the inside of a subject, that is, the inside of a living body. Furthermore, in a case where the moving image 38 and the still image 39 are each an image acquired by using light in the above-described specific wavelength range (special light), both the images are special-light images. The endoscope processor apparatus 12 outputs the generated moving image 38 and still image 39 to each of the display apparatus 13 and the medical image processing apparatus 14.

The endoscope processor apparatus 12 may generate (acquire) a special-light image having information of the above-described specific wavelength range on the basis of a normal-light image acquired by using the above-described white light. In this case, the endoscope processor apparatus 12 functions as a special-light image acquiring unit. The endoscope processor apparatus 12 acquires a signal in the specific wavelength range by performing computation based on RGB color information of red, green, and blue or CMY color information of cyan, magenta, and yellow included in the normal-light image.

The endoscope processor apparatus 12 may generate a feature-quantity image, such as a known oxygen saturation image, for example, on the basis of at least one of a normal-light image acquired by using the above-described white light or a special-light image acquired by using the above-described light in the specific wavelength range (special light). In this case, the endoscope processor apparatus 12 functions as a feature-quantity image generating unit. The moving image 38 or the still image 39, including the above-described inside-of-living-body image, normal-light image, special-light image, and feature-quantity image, is a medical image generated through imaging of a result of capturing an image of a human body or measuring the human body for the purpose of diagnosis or examination using the image.

The display apparatus 13 is connected to the endoscope processor apparatus 12 and displays the moving image 38 and the still image 39 received from the endoscope processor apparatus 12. A user performs, for example, an operation of moving the insertion section 20 forward or backward while viewing the moving image 38 displayed on the display apparatus 13. When the user finds a lesion or the like in a portion that is being observed, the user operates the still image capturing instruction unit 32 and captures a still image of the portion that is being observed, or performs diagnosis, biopsy, or the like.

The medical image processing apparatus 14 is an apparatus capable of automatically recognizing and automatically discriminating a lesion as a region of interest. The medical image processing apparatus 14 is an apparatus that reports a region of interest included in a medical image to a user and that facilitates observation of the boundary (demarcation line) between the region of interest and a region of non-interest other than the region of interest. As the medical image processing apparatus 14, a personal computer is used, for example. As the operation unit 15, a keyboard, a mouse, and the like connected to the personal computer in a wired or wireless manner are used. As the display 16 (an example of a reporting unit), a monitor of various types, such as a liquid crystal monitor, connectable to the personal computer is used.

The medical image processing apparatus 14 and the display 16 (an example of a first display unit) function as a diagnosis support apparatus that displays the moving image 38 and a figure for reporting a region of interest included in the moving image 38 on the display 16.

Configuration of Medical Image Processing Apparatus

Figure 2:
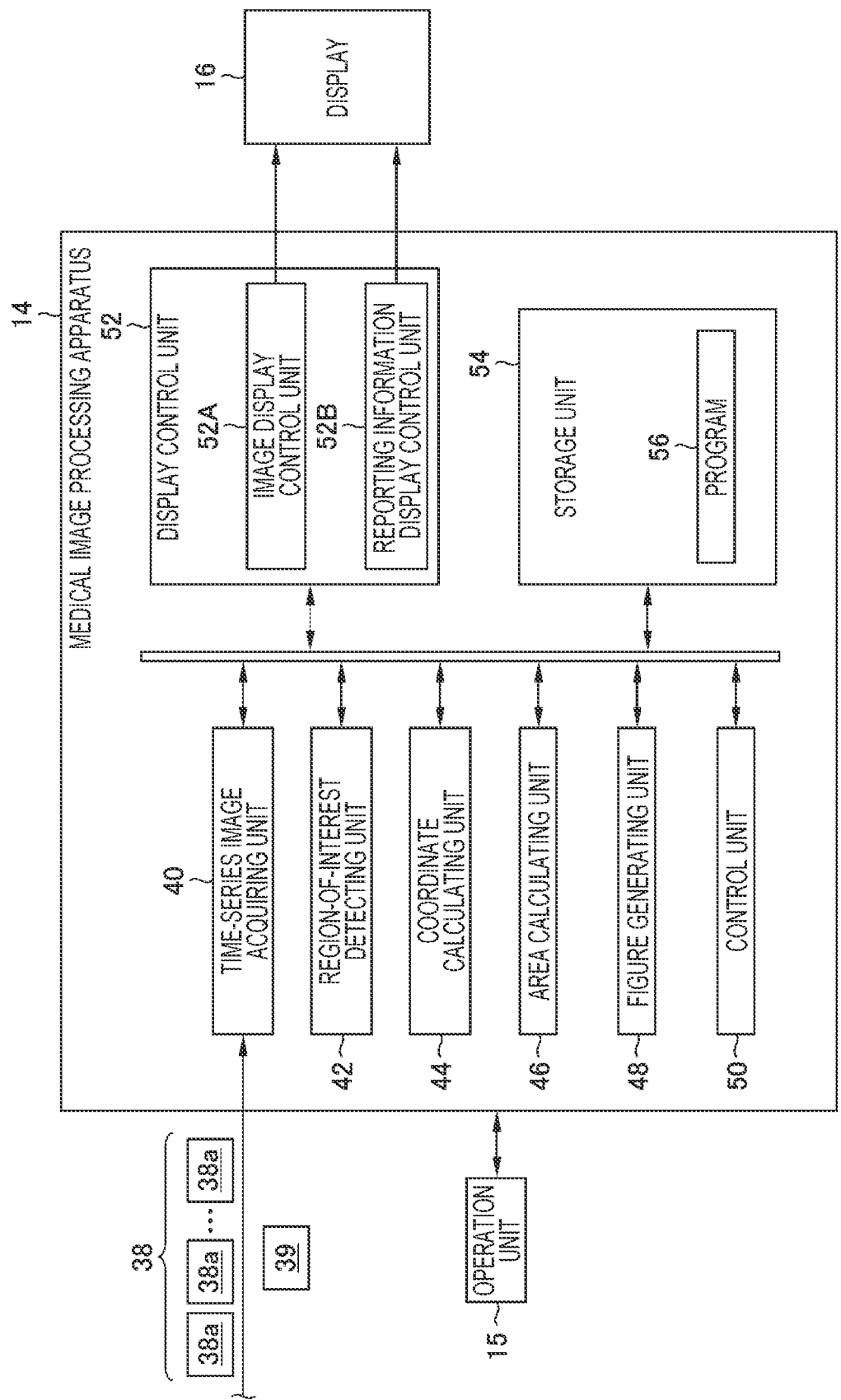
FIG. 2 is a block diagram illustrating an example of an electric configuration of the medical image processing apparatus.

FIG. 2 is a block diagram illustrating an example of an electric configuration of the medical image processing apparatus 14. The medical image processing apparatus 14 illustrated in FIG. 2 is constituted mainly by a time-series image acquiring unit 40, a region-of-interest detecting unit 42, a coordinate calculating unit 44, an area calculating unit 46, a figure generating unit 48, a control unit 50, a display control unit 52, and a storage unit 54.

The control unit 50 centrally controls the time-series image acquiring unit 40, the region-of-interest detecting unit 42, the coordinate calculating unit 44, the area calculating unit 46, the figure generating unit 48, and the display control unit 52, and functions as part of these units, on the basis of a program (medical image processing program) 56 stored in the storage unit 54.

The storage unit 54 is a storage device, such as a hard disk device. The storage unit 54 stores a detection result of the region-of-interest detecting unit 42 and the still image 39 that has been captured, and also stores the program 56 and information or the like related to various types of control of the medical image processing apparatus 14.

The time-series image acquiring unit 40 sequentially acquires endoscopic images as an example of medical images. Here, the time-series image acquiring unit 40 acquires the moving image 38 (in this example, the moving image 38 captured by the endoscope 10) made up of the time-series frame images 38a from the endoscope processor apparatus 12 by using an image input/output interface that is connected to the endoscope processor apparatus 12 (see FIG. 1) in a wired or wireless manner and that is not illustrated. In a case where the endoscope 10 captures the above-described still image 39 while capturing the moving image 38, the time-series image acquiring unit 40 acquires the moving image 38 and the still image 39 from the endoscope processor apparatus 12.

The time-series image acquiring unit 40 may acquire the moving image 38 via an information storage medium of various types, such as a memory card or a hard disk device, instead of directly acquiring the moving image 38 from the endoscope processor apparatus 12. Alternatively, the time-series image acquiring unit 40 may acquire the moving image 38 uploaded to a server, a database, or the like on the Internet, via the Internet.

The region-of-interest detecting unit 42 is an example of a region-of-interest information acquiring unit that acquires region-of-interest information from a medical image, and detects a region of interest from the moving image 38 captured during observation of the inside of a subject. The region-of-interest detecting unit 42 includes a convolutional neural network (CNN) that calculates a feature quantity of each of the frame images 38a (or thinned out frame images 38a at regular intervals) of the moving image 38 and that recognizes a region of interest in the image.

Examples of a region of interest include a polyp, a cancer, a colon diverticulum, an inflammation, a scar of endoscopic mucosal resection (EMR), a scar of endoscopic submucosal dissection (ESD), a clip portion, a bleeding point, a perforation, angiodysplasia, a treatment tool, and the like.

The region-of-interest detecting unit 42 is capable of acquiring a recognition result of category classification or the like indicating a category to which a detected region of interest belongs among a plurality of categories related to a lesion, such as "neoplastic", "non-neoplastic", and "others".

The region-of-interest detecting unit 42 is not limited to a unit that detects a region of interest by using a CNN, and may be a unit that detects a region of interest by performing image processing to analyze a feature quantity, such as a color, pixel value gradient, shape, or size in an image.

The coordinate calculating unit 44 is an example of a region-of-interest information acquiring unit, and calculates the coordinates indicating the position in a frame image 38a of a region of interest detected by the region-of-interest detecting unit 42. Here, the coordinate calculating unit 44 calculates the coordinates of the position on which a figure for reporting the region of interest is to be superimposed. The coordinates of the position of superimposition is, for example, the coordinates of the boundary between the region of interest and a region of non-interest other than the region of interest, the coordinates of a position that is inside the region of interest and along the boundary, or the coordinates of the center of gravity of the region of interest.

The area calculating unit 46 is an example of a region-of-interest information acquiring unit, and calculates the area on an image of a region of interest detected by the region-of-interest detecting unit 42. The area of the region of interest may be the area of the region of interest or the area of a rectangle, a polygon, or a circle in which the region of interest is inscribed. The area calculating unit 46 may calculate the circumference of the region of interest instead of the area of the region of interest.

The figure generating unit 48 generates a figure for reporting a region of interest to a user. The figure generated by the figure generating unit 48 will be described below.

The display control unit 52 is an example of a superimposition processing unit that superimposes a figure on a medical image, and causes the display 16 to display a medical image on which a figure is superimposed. The display control unit 52 includes an image display control unit 52A and a reporting information display control unit 52B.

The image display control unit 52A outputs the moving image 38 acquired by the time-series image acquiring unit 40 to the display 16 and causes the display 16 to display the moving image 38. That is, a plurality of frame images 38a are sequentially displayed on the display 16.

The reporting information display control unit 52B superimposes a figure generated by the figure generating unit 48 on the position of coordinates calculated by the coordinate calculating unit 44 of the frame image 38a displayed on the display 16. Accordingly, the reporting information display control unit 52B superimposes the figure on an inside of a region of interest such that at least part of the boundary between the region of interest and a region of non-interest is not superimposed with the figure.

Here, the reporting information display control unit 52B causes at least 50% of the boundary not to be superimposed with the figure. Preferably, the reporting information display control unit 52B causes 95% of the boundary not to be superimposed with the figure. More preferably, the reporting information display control unit 52B causes 100% of the boundary not to be superimposed with the figure.

In this way, the region of interest is reported by superimposing the figure on the inside of the region of interest such that at least part of the boundary between the region of interest and the region of non-interest is not hidden by the figure. Thus, it is possible to cause a user to visually recognize the boundary.

Medical Image Processing Method

Next, a medical image processing method according to the present embodiment will be described. The medical image processing method is performed as a result of execution of the program 56 stored in the storage unit 54 by the control unit 50.

Figure 3:
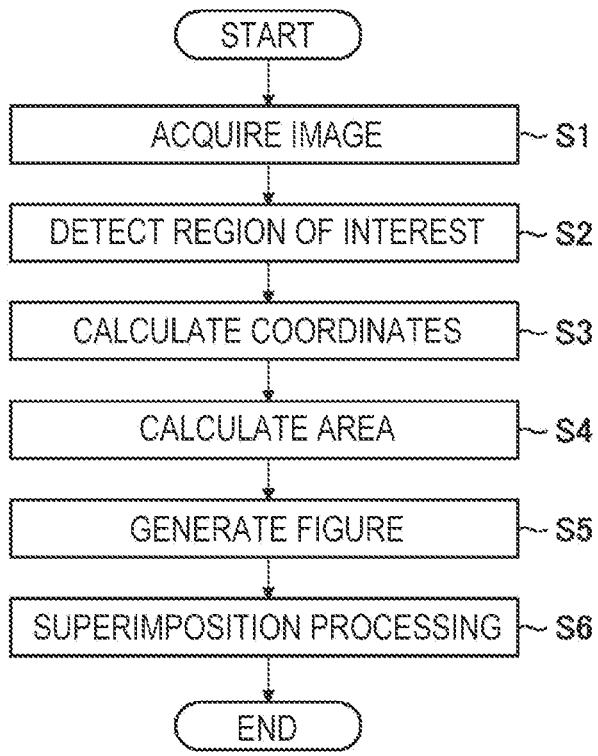
FIG. 3 is a flowchart illustrating an example of individual steps in a medical image processing method.

FIG. 3 is a flowchart illustrating an example of individual steps in the medical image processing method. The medical image processing method includes an image acquisition step (step S1), a region-of-interest detection step (step S2), a coordinate calculation step (step S3), an area calculation step (step S4), a figure generation step (step S5), and a superimposition processing step (step S6).

In step S1, the time-series image acquiring unit 40 acquires a frame image 38a of the moving image 38. In step S2, the region-of-interest detecting unit 42 detects a region of interest from the frame image 38a acquired in step S1.

In step S3, the coordinate calculating unit 44 calculates the coordinates indicating the position in an image of the region of interest detected in step S2. In step S4, the area calculating unit 46 calculates the area on the image of the region of interest detected in step S2.

In step S5, the figure generating unit 48 generates a figure for reporting the region of interest detected in step S2 to a user. The figure generating unit 48 generates a figure having an area smaller than the area calculated in step S4.

In step S6, the display control unit 52 superimposes the figure generated in step S5 on the positon of the coordinates calculated in step S3 of the frame image 38a acquired in step S1, and causes the display 16 to display the frame image 38a on which the figure is superimposed. Accordingly, the figure is superimposed on the inside of the region of interest detected in step S2. This figure is smaller than the area of the region of interest calculated in step S4, and thus at least part of the boundary between the region of interest and a region of non-interest is not superimposed with the figure.

As described above, according to the medical image processing method, it is possible to report a region of interest without hindering observation of the boundary between the region of interest and a region of non-interest in a medical image.

Examples of Figure

The details of a figure superimposed on a region of interest will be described. A figure to be superimposed on a region of interest may be stored in the storage unit 54 in advance instead of being generated by the figure generating unit 48.

Manner of Pointing to Boundary

A figure superimposed on a region of interest is preferably a figure that shows a user the position of the boundary between the region of interest and a region of non-interest. Hereinafter, the boundary between a region of interest and a region of non-interest will be simply referred to as the boundary of a region of interest.

Figure 4:
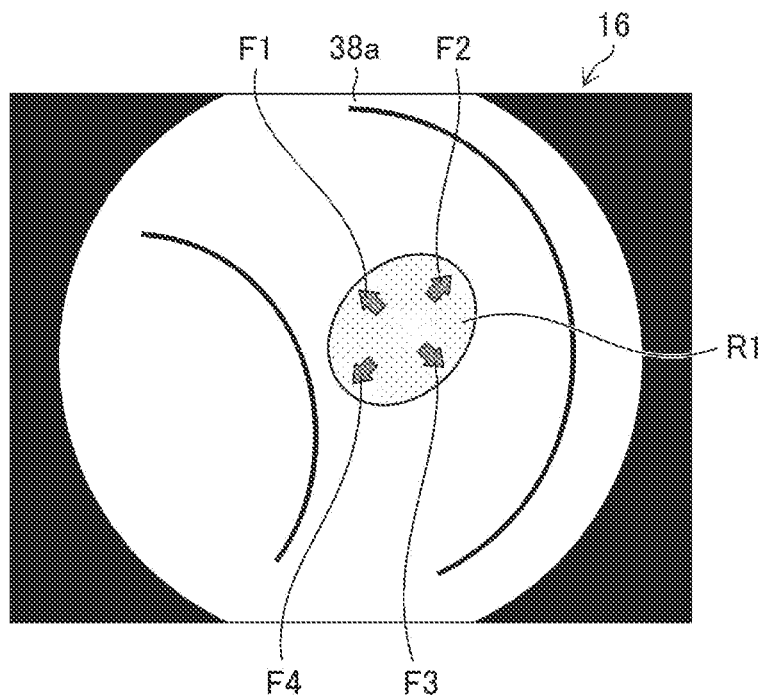
FIG. 4 is a diagram illustrating an example of display on a display.
Figure 5:
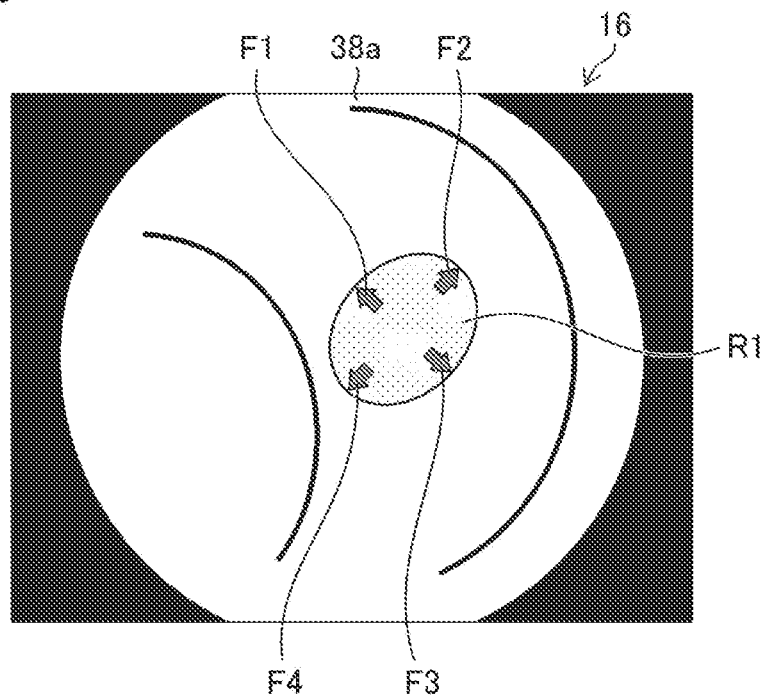
FIG. 5 is a diagram illustrating an example of display on the display.

FIG. 4 and FIG. 5 are each a diagram illustrating an example of display on the display 16. In this example, a frame image 38a including a region of interest R1 is displayed. Four figures which are a figure F1, a figure F2, a figure F3, and a figure F4 are superimposed on the inside of the region of interest R1.

The figure F1, the figure F2, the figure F3, and the figure F4 are figures having the same arrow shape. The figure F1, the figure F2, the figure F3, and the figure F4 each have an area smaller than the area of the region of interest R1. The figure F1, the figure F2, the figure F3, and the figure F4 have the same color.

The figure F1, the figure F2, the figure F3, and the figure F4 are each oriented to point to, at the tip of the arrow, the boundary of the region of interest R1. Here, the figure F1, the figure F2, the figure F3, and the figure F4 are each oriented such that the direction of the arrow vertically intersects the direction of a tangent to the boundary at a point of contact between the extension line of the arrow and the boundary.

FIG. 4 illustrates an example in which the figure F1, the figure F2, the figure F3, and the figure F4 are each located at a position where the tip of the arrow is not in contact with the boundary of the region of interest R1. In this case, the coordinate calculating unit 44 calculates the coordinates of positions inside the region of interest R1 and along the boundary of the region of interest R1. The figure generating unit 48 generates the figure F1, the figure F2, the figure F3, and the figure F4 each of which is a figure having an arrow shape and oriented in accordance with the calculated coordinates. The reporting information display control unit 52B superimposes the figure F1, the figure F2, the figure F3, and the figure F4 on the region of interest R1 such that the tips of the respective arrows match the calculated coordinates.

FIG. 5 illustrates an example in which the figure F1, the figure F2, the figure F3, and the figure F4 are each located at a position where the tip of the arrow is in contact with the boundary of the region of interest R1. In this case, the coordinate calculating unit 44 calculates the coordinates on the boundary of the region of interest R1. The figure generating unit 48 generates the figure F1, the figure F2, the figure F3, and the figure F4 each of which is a figure having an arrow shape and oriented in accordance with the calculated coordinates. The reporting information display control unit 52B superimposes the figure F1, the figure F2, the figure F3, and the figure F4 on the inside of the region of interest R1 such that the tips of the respective arrows match the calculated coordinates.

As a result of superimposing figures on a region of interest such that at least part of the boundary between the region of interest and a region of non-interest is not superimposed with the figures as in FIG. 4 and FIG. 5, it is possible to report the region of interest without hindering observation of the boundary between the region of interest and the region of non-interest in a medical image. Thus, a user is able to easily observe the boundary between a lesion portion as a region of interest and a normal mucous membrane portion other than the lesion portion.

Figure 6:
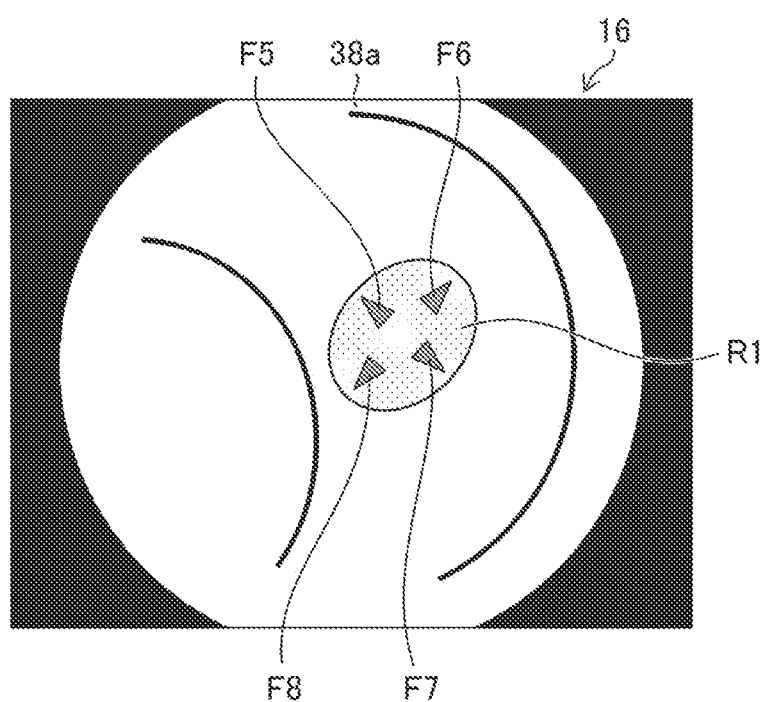
FIG. 6 is a diagram illustrating an example of display on the display.

The superimposed figure is not limited to an arrow, and any figure clearly pointing to the boundary between a region of interest and a region of non-interest may be used. FIG. 6 is a diagram illustrating an example of display on the display 16. In this example, four figures which are a figure F5, a figure F6, a figure F7, and a figure F8 are superimposed on the inside of the region of interest R1 included in the frame image 38a.

The figure F5, the figure F6, the figure F7, and the figure F8 are figures having the same isosceles triangle shape. An isosceles triangle has a base that is shorter than two equal sides. The figure F5, the figure F6, the figure F7, and the figure F8 have the same size and color and have different orientations.

The figure F5, the figure F6, the figure F7, and the figure F8 are each oriented to point to, at the vertex shared between the two equal sides of the isosceles triangle, the boundary of the region of interest R1. Here, the figure F5, the figure F6, the figure F7, and the figure F8 are each oriented such that the direction of the normal to the base passing the vertex of the isosceles triangle vertically intersects the direction of a tangent to the boundary at a point of contact between the extension line of the normal and the boundary of the region of interest R1.

The coordinate calculating unit 44 calculates the coordinates of positions inside the region of interest R1 and along the boundary of the region of interest R1. The figure generating unit 48 generates the figure F5, the figure F6, the figure F7, and the figure F8 each of which is a figure having an isosceles triangle shape and oriented in accordance with the calculated coordinates. The reporting information display control unit 52B superimposes the figure F5, the figure F6, the figure F7, and the figure F8 on the region of interest R1 such that the vertexes of the respective isosceles triangles match the calculated coordinates.

As a result of superimposing figures on a region of interest in this manner, it is possible to report the region of interest without hindering observation of the boundary between the region of interest and a region of non-interest in a medical image. Thus, a user is able to easily observe the boundary between a lesion portion as a region of interest and a normal mucous membrane portion.

Manner of Representing Inside Coordinates

A figure superimposed on a region of interest is not limited to a figure pointing to the boundary, and may be a figure representing coordinates in the inside of the region of interest. For example, a figure may be located such that certain coordinates in the inside of the region of interest matches the center of the figure.

Figure 7:
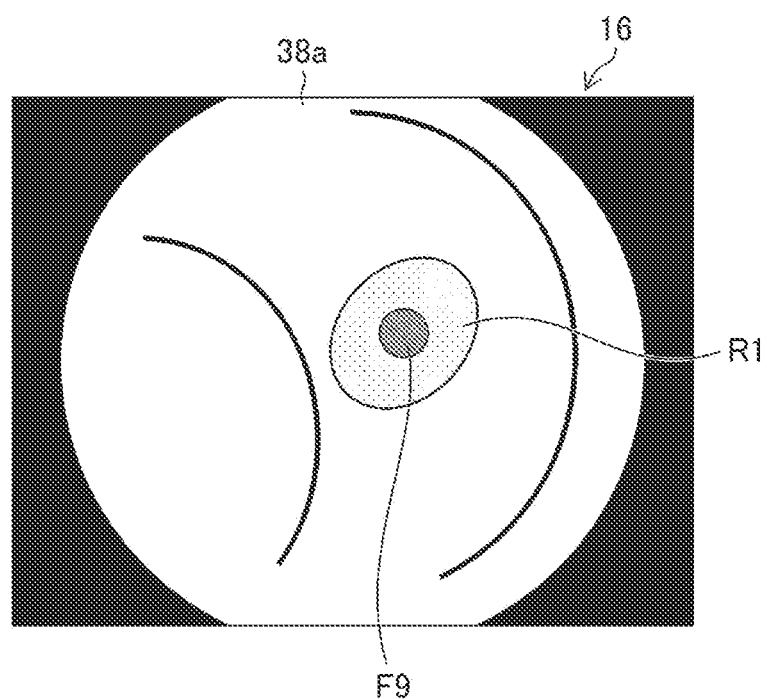
FIG. 7 is a diagram illustrating an example of display on the display.

FIG. 7 is a diagram illustrating an example of display on the display 16. In this example, a frame image 38a including the region of interest R1 is displayed. A single figure F9 is superimposed on the inside of the region of interest R1.

The figure F9 is a figure having a circle shape. The figure F9 has an area smaller than the area of the region of interest R1. The figure F9 is located such that the center of the figure F9 matches certain coordinates in the inside of the region of interest R1.

The coordinate calculating unit 44 calculates the coordinates of a certain position inside the region of interest R1. The figure generating unit 48 generates the figure F9 having a circle shape. The reporting information display control unit 52B superimposes the figure F9 on the region of interest R1 such that the center of gravity of the figure F9 matches the calculated coordinates.

As a result of superimposing a figure on a region of interest in this manner, it is possible to report the region of interest without hindering observation of the boundary between the region of interest and a region of non-interest in a medical image. Thus, a user is able to easily observe the boundary between a lesion portion as a region of interest and a normal mucous membrane portion.

Figure 8:
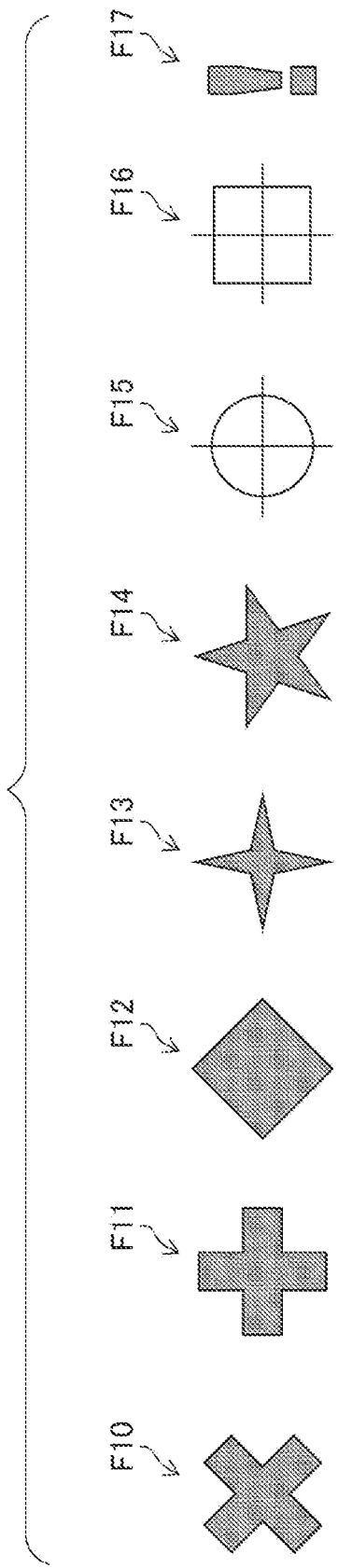
FIG. 8 is a diagram illustrating other examples of a figure.
Figure 9:
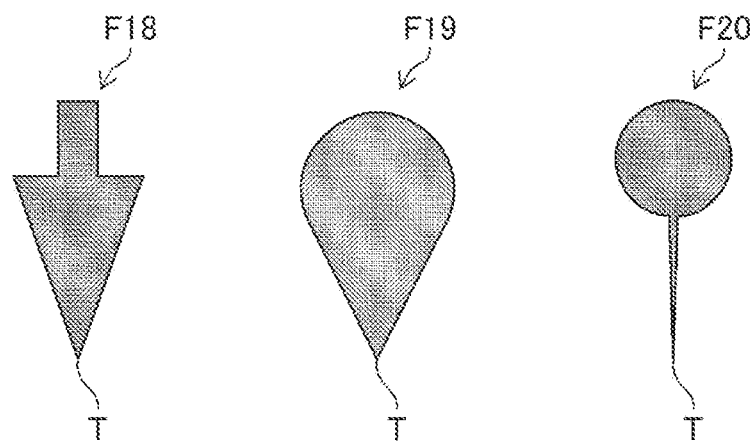
FIG. 9 is a diagram illustrating other examples of a figure.

Although the figure F9 that is circular is superimposed in the example illustrated in FIG. 7, the shape of the figure superimposed on the coordinates of a certain position is not limited to circular. FIG. 8 and FIG. 9 are diagrams illustrating other examples of a figure. As illustrated in FIG. 8, a tilted-cross-shaped figure F10, a cross-shaped figure F11, a tilted-square-shaped figure F12, a four-vertex-star-shaped figure F13, a five-vertex-star-shaped figure F14, a circle-and-cross figure F15, a rectangle-and-cross figure F16, an exclamation-mark-shaped figure F17, or the like may be used. Other symbols or characters may also be used. As a result of superimposing such a figure such that the center of gravity of the figure matches the coordinates of a certain position inside a region of interest, it is possible to report the region of interest without hindering observation of the boundary between the region of interest and a region of non-interest in a medical image.

As illustrated in FIG. 9, an arrow-shaped figure F18 having a tip T, a drop-shaped figure F19 having a tip T, or a pin-shaped figure F20 having a tip T may be used. In this case, as a result of superimposing such a figure such that the tip T of the figure matches the coordinates of a certain position inside a region of interest, it is possible to report the region of interest without hindering observation of the boundary between the region of interest and a region of non-interest in a medical image.

Figure 10:
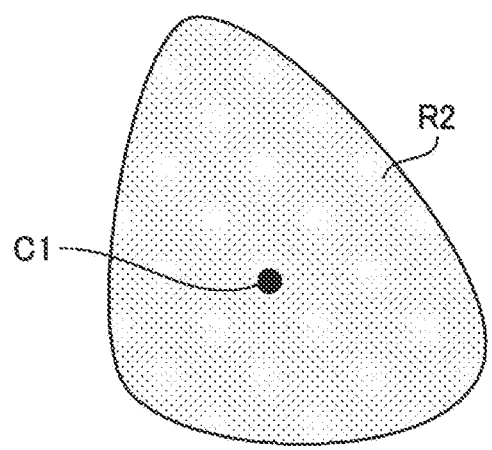
FIG. 10 is a diagram illustrating the center of gravity of a region of interest.
Figure 11:
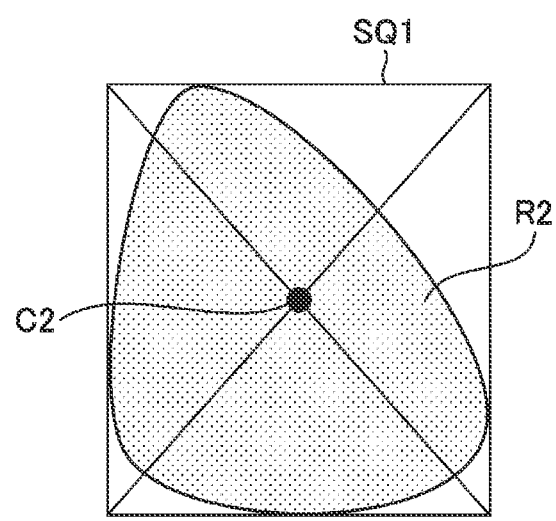
FIG. 11 is a diagram illustrating the center of a rectangle circumscribing a region of interest.

The coordinates of a certain point may be the coordinates of the center of gravity (centroid) of the region of interest, the coordinates of the center of a rectangle circumscribing the region of interest, or the like. FIG. 10 is a diagram illustrating a center of gravity C1 of a region of interest R2. FIG. 11 is a diagram illustrating a center C2 of a rectangle SQ1 circumscribing the region of interest R2.

In this way, as a result of superimposing a figure on the center of gravity C1 or the center C2 of the region of interest R2, it is possible to report the region of interest without hindering observation of the boundary between the region of interest and a region of non-interest in a medical image.

Manner of Changing Size in Accordance with Size of Region of Interest

The size of a figure superimposed on a region of interest is not necessarily fixed. For example, the figure generating unit 48 may change the size of a figure to be generated in accordance with the size of the region of interest in an image. Here, the size of the figure is an index that is proportional to the area of the figure.

Figure 12:
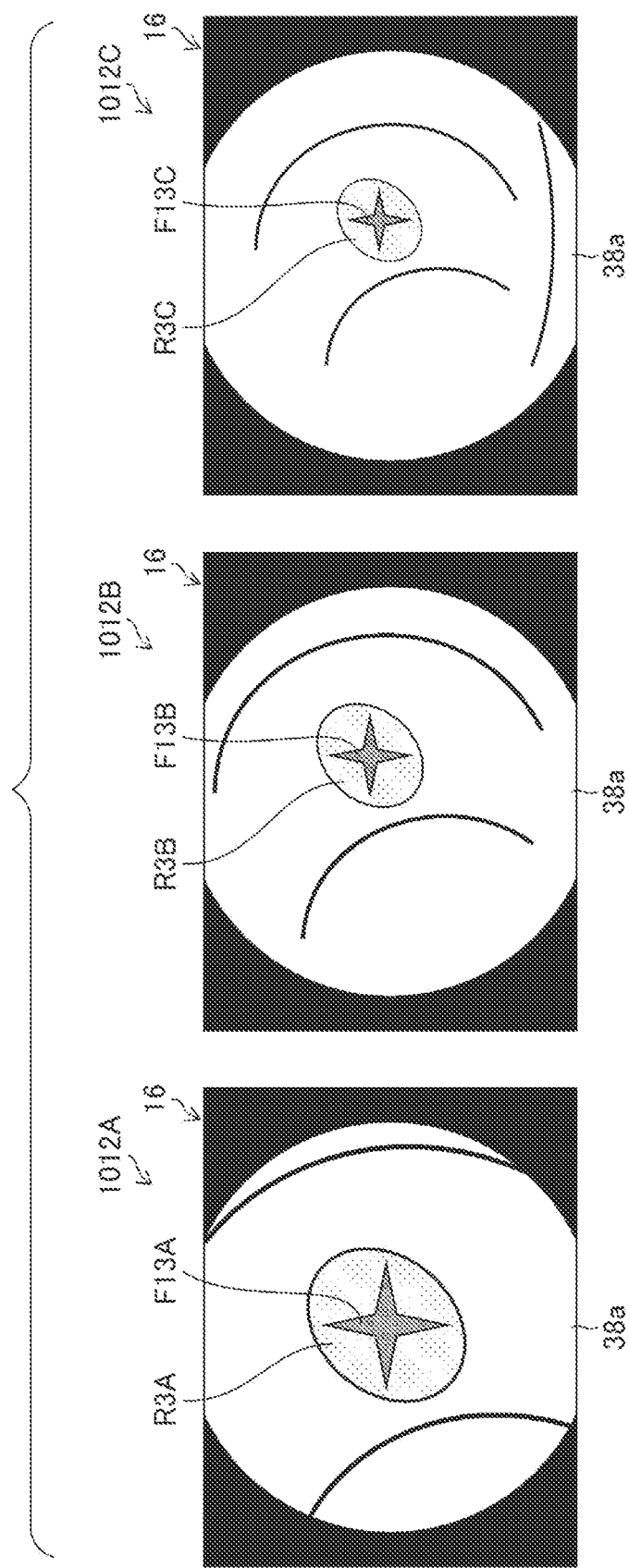
FIG. 12 is a diagram illustrating examples of display on the display.

FIG. 12 is a diagram illustrating examples of display on the display 16. In parts 1012A, 1012B, and 1012C illustrated in FIG. 12, the frame images 38a respectively including a region of interest R3A, a region of interest R3B, and a region of interest R3C are displayed. Here, the relationship "the area of the region of interest R3A>the area of the region of interest R3B>the area of the region of interest R3C" is satisfied.

Four-vertex-star-shaped figures F13A, F13B, and F13C are superimposed on the region of interests R3A, R3B, and R3C, respectively. Here, the relationship "the size of the figure F13A>the size of the figure F13B>the size of the figure F13C" is satisfied.

In this way, as a result of increasing the size of the figure to be superimposed as the area of the region of interest increases, it is possible to report the region of interest without hindering observation of the boundary between the region of interest and a region of non-interest in a medical image.

In a case where a region of interest is significantly large, there is a high possibility that a user is observing the details of the region of interest. Thus, if a figure of a relatively large size corresponding to the area of the region of interest is superimposed on the region of interest, the superimposed figure may disturb the user. Thus, in a case where the area of the region of interest is larger than or equal to a first area, the figure generating unit 48 generates a figure having a fixed first size without increasing the size of the figure any more.

Figure 13:
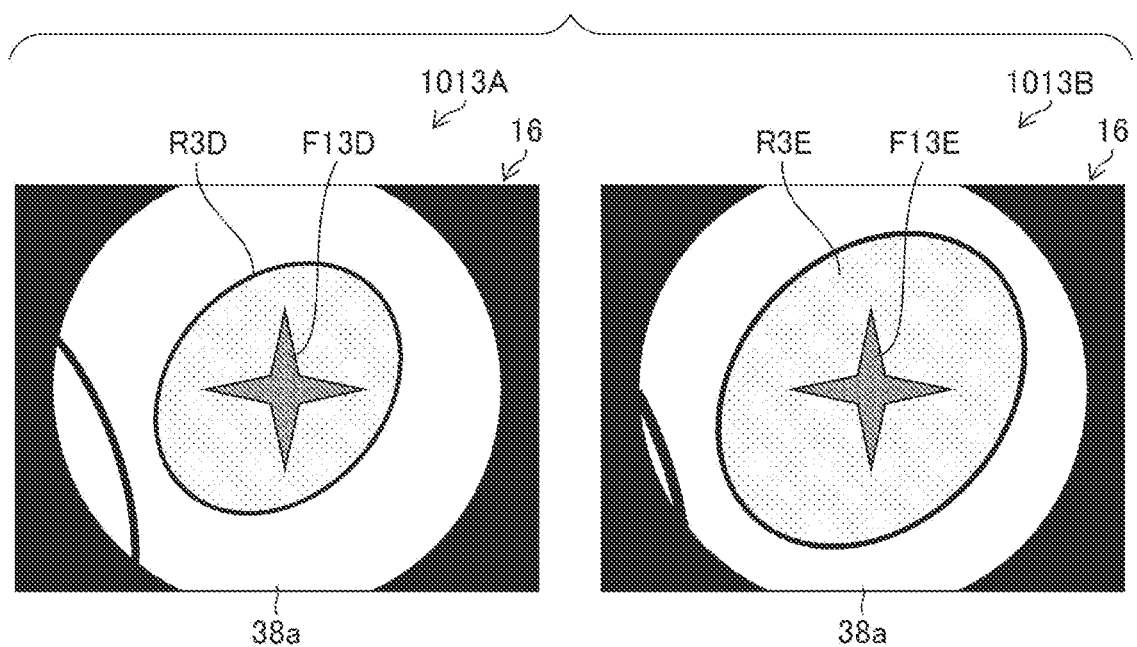
FIG. 13 is a diagram illustrating examples of display on the display.

FIG. 13 is a diagram illustrating examples of display on the display 16. In parts 1013A and 1013B illustrated in FIG. 13, the frame images 38a respectively including a region of interest R3D and a region of interest R3E are displayed. Here, the relationship "the area of the region of interest R3A<the first area<the area of the region of interest R3D<the area of the region of interest R3E" is satisfied.

Four-vertex-star-shaped figures F13D and F13E are superimposed on the region of interests R3D and R3E, respectively. Here, the relationship "the size of the figure F13A<the size of the figure F13D=the size of the figure F13E" is satisfied.

In this way, as a result of not changing, that is, fixing the size of the figure to be superimposed in a case where the area of the region of interest is larger than or equal to the first area, it is possible to appropriately report the region of interest even in a case where the region of interest is significantly large.

In a case where the size of the figure is changed in accordance with the area of the region of interest and in a case where the region of interest is significantly small, the size of the figure may become too small and the performance of reporting to the user degrades. Thus, in a case where the area of the region of interest is smaller than or equal to a second area, the figure generating unit 48 generates a figure having a fixed second size without decreasing the size of the figure any more.

Figure 14:
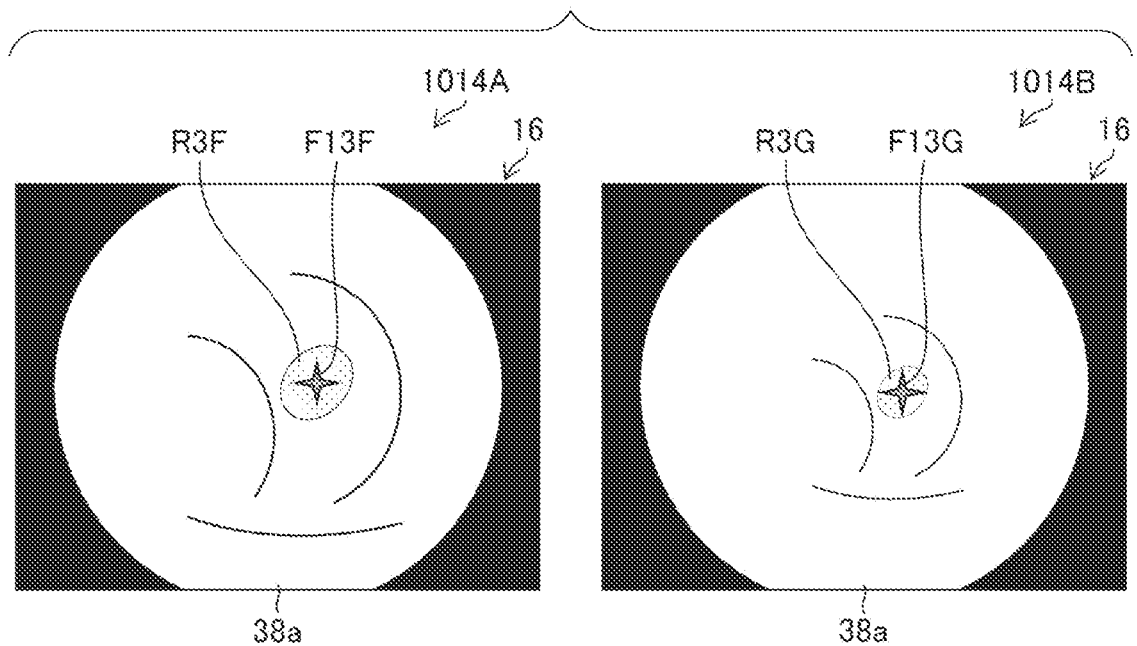
FIG. 14 is a diagram illustrating examples of display on the display.

FIG. 14 is a diagram illustrating examples of display on the display 16. In parts 1014A and 1014B illustrated in FIG. 14, the frame images 38a respectively including a region of interest R3F and a region of interest R3G are displayed. Here, the relationship "the area of the region of interest R3C>the second area>the area of the region of interest R3F>the area of the region of interest R3G" is satisfied.

Four-vertex-star-shaped figures F13F and F13G are superimposed on the region of interests R3F and R3G, respectively. Here, the relationship "the size of the figure F13C>the size of the figure F13F=the size of the figure F13G" is satisfied.

In this way, as a result of fixing the size of the figure to be superimposed in a case where the area of the region of interest is smaller than or equal to the second area, it is possible to appropriately report the region of interest even in a case where the region of interest is significantly small.

Manner of Changing Shape in Accordance with Size of Region of Interest

Figure 15:
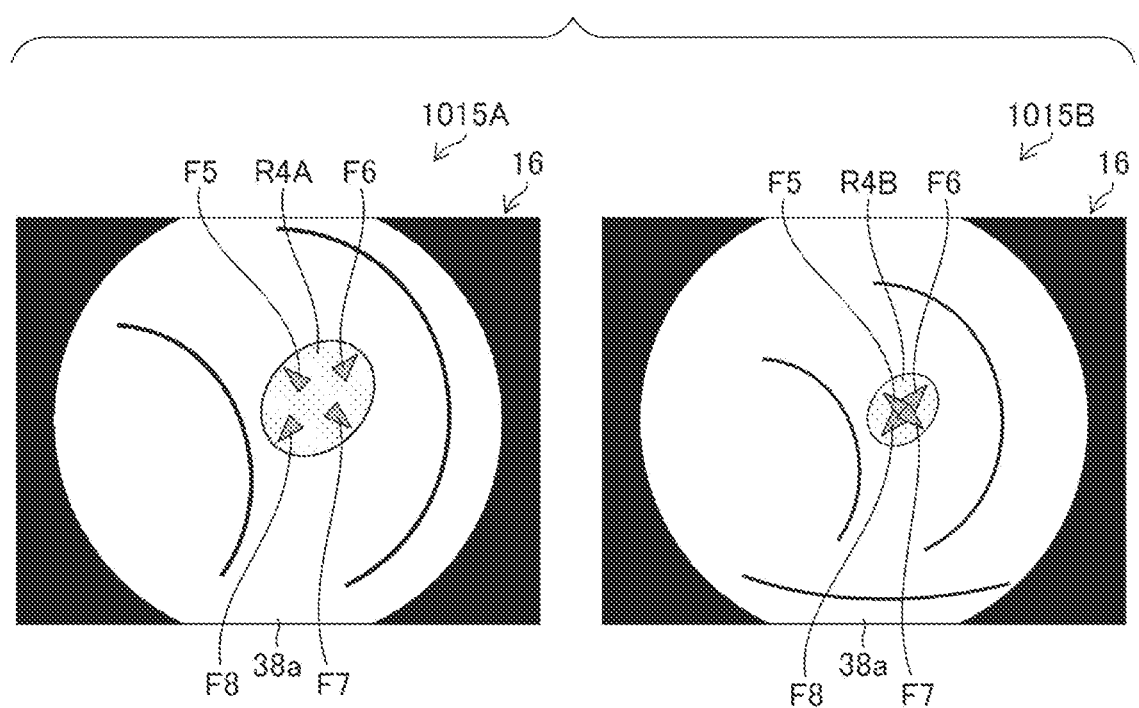
FIG. 15 is a diagram illustrating examples of display on the display.

FIG. 15 is a diagram illustrating examples of display on the display 16. In parts 1015A and 1015B illustrated in FIG. 15, the frame images 38a respectively including a region of interest R4A and a region of interest R4B are displayed. Here, the relationship "the area of the region of interest R4A>the area of the region of interest R4B" is satisfied.

The figure F5, the figure F6, the figure F7, and the figure F8 are superimposed on each of the region of interest R4A and the region of interest R4B.

As illustrated in part 1015B, in a case where a region of interest has a small area in an image, such as the region of interest R4B, the figure F5, the figure F6, the figure F7, and the figure F8 superimposed on the region of interest R4B overlap each other and degrades the visibility of the region of interest.

To prevent this, the shape of a figure superimposed on a region of interest is not necessarily fixed. For example, the figure generating unit 48 may change the shape of a figure to be generated in accordance with the size of a region of interest in an image. Here, a description will be given of an example of changing the shape of a figure by using, as a threshold value, a certain fixed third area of a region of interest.

Figure 16:
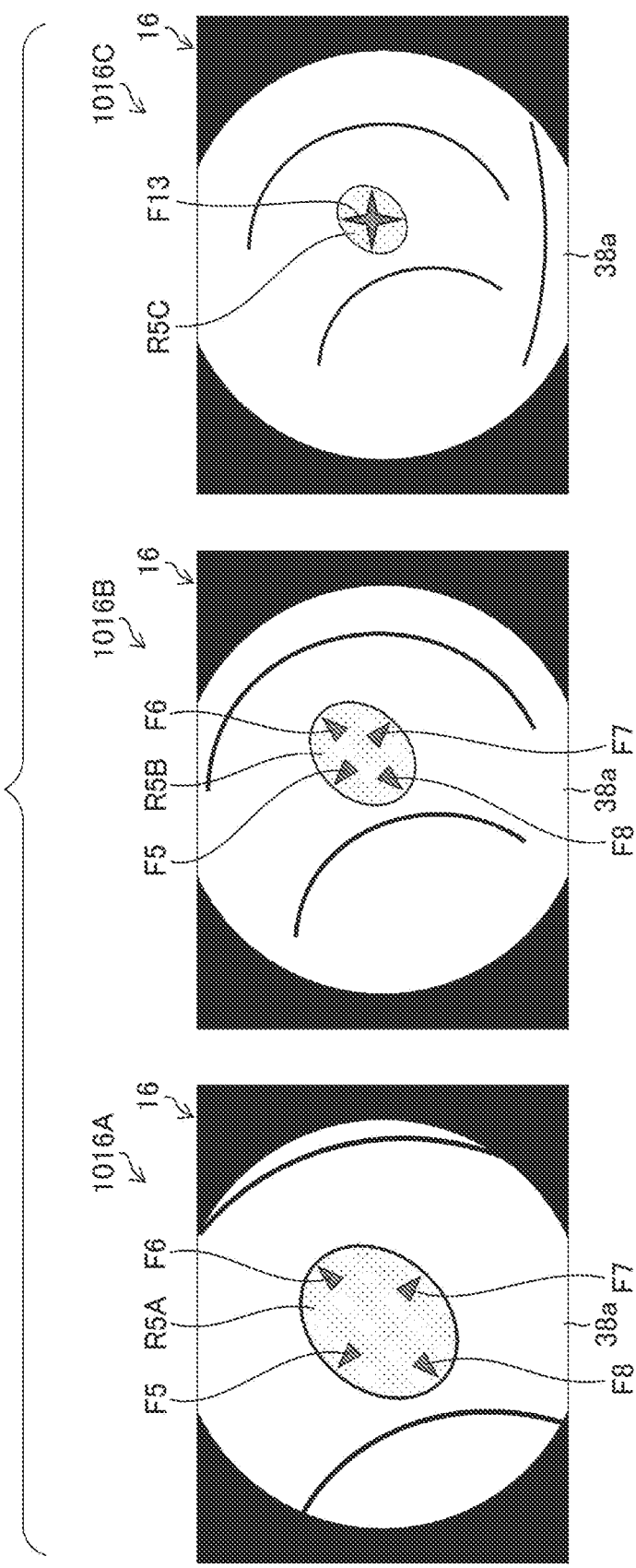
FIG. 16 is a diagram illustrating examples of display on the display.

FIG. 16 is a diagram illustrating examples of display on the display 16. In parts 1016A, 1016B, and 1016C illustrated in FIG. 16, the frame images 38a respectively including a region of interest R5A, a region of interest R5B, and a region of interest R5C are displayed. Here, the relationship "the area of the region of interest R5A>the area of the region of interest R5B>the third area>the area of the region of interest R5C" is satisfied.

As illustrated in FIG. 16, the figure F5, the figure F6, the figure F7, and the figure F8 are superimposed on each of the region of interest R5A and the region of interest R5B whose area is larger than or equal to the third area. On the other hand, a figure F13 is superimposed on the region of interest R5C whose area is smaller than the third area.

In this way, in a case where a region of interest has an area larger than or equal to the certain fixed third area, a figure located inside the region of interest and pointing to the boundary of the region of interest is displayed, and in a case where a region of interest has an area smaller than the third area, a figure representing the coordinates in the inside of the region of interest is displayed. In this display manner, in a case where a region of interest is relatively large, the center of the region of interest and a normal mucous membrane near the boundary of the region of interest can be easily observed. In a case where a region of interest is relatively small, a simpler figure is displayed, so that observation by a user is not hindered.

In a case where a region of interest has an area smaller than a certain fixed fourth area, the figure generating unit 48 may generate a figure surrounding the region of interest.

Figure 17:
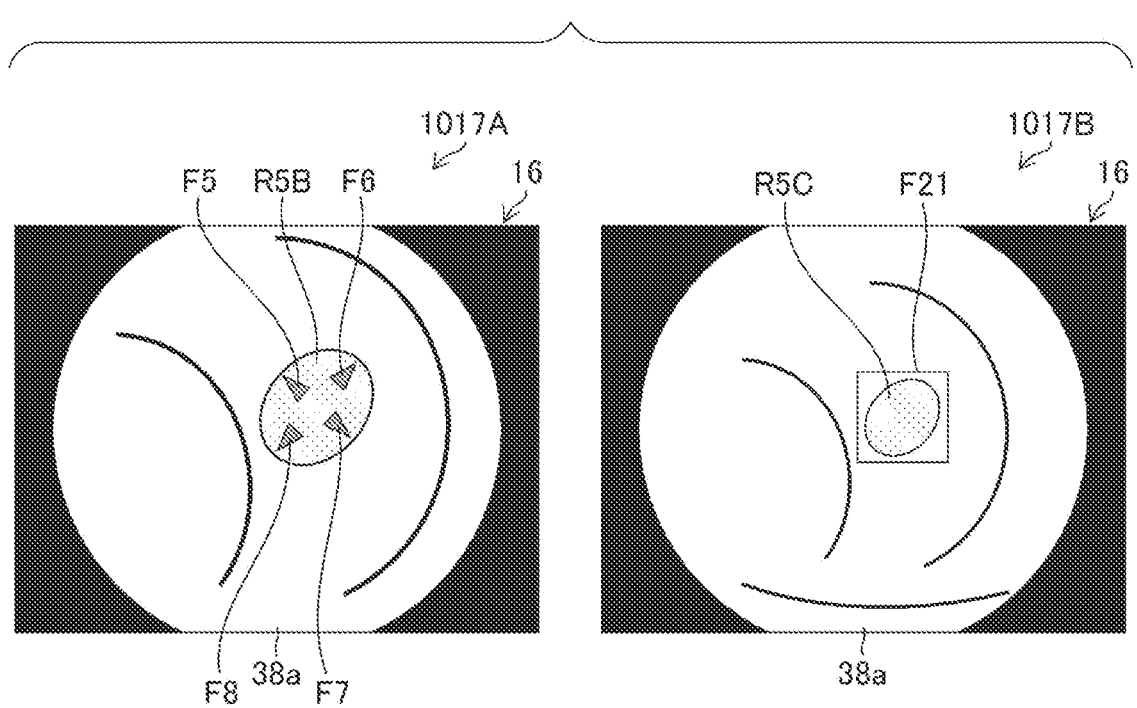
FIG. 17 is a diagram illustrating examples of display on the display.

FIG. 17 is a diagram illustrating examples of display on the display 16. In parts 1017A and 1017B illustrated in FIG. 17, the frame images 38a respectively including the region of interest R5B and the region of interest R5C are displayed. Here, the relationship "the area of the region of interest R5B>the fourth area>the area of the region of interest R5C" is satisfied.

As illustrated in FIG. 17, the figure F5, the figure F6, the figure F7, and the figure F8 are superimposed on the region of interest R5B whose area is larger than or equal to the fourth area. On the other hand, a figure F21, which is a rectangle surrounding the region of interest R5C, is superimposed around the region of interest R5C whose area is smaller than the fourth area.

As a result of surrounding the region of interest, the visibility of the boundary of the region of interest and a normal mucous membrane near the region of interest decreases. However, in a case where the region of interest has a significantly small area, it is more important to notify the user of the presence of the region of interest than to improve the visibility of the surroundings of the region of interest. Thus, it is desired to adopt the display method illustrated in FIG. 17. In this display manner, in a case where a region of interest is relatively large, the center of the region of interest and a normal mucous membrane near the boundary of the region of interest can be easily observed. In a case where a region of interest is relatively small, it is possible to cause the user to recognize the region of interest.

The figure surrounding the region of interest is not limited to a rectangle, and any figure indicating a range of the region of interest from the outside of the region of interest may be used.

Figure 18:
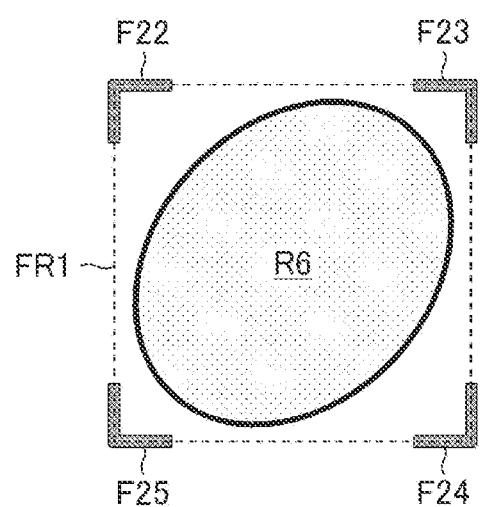
FIG. 18 is a diagram illustrating four figures surrounding a region of interest.

FIG. 18 is a diagram illustrating four figures which are a figure F22, a figure F23, a figure F24, and a figure F25 surrounding a region of interest R6. The figure F22 is an L-shaped figure made up of a horizontal line segment and a vertical line segment. The figure F23, the figure F24, and the figure F25 are each a figure having the same shape as the figure F22 and having orientation different from the figure F22. The figure F22, the figure F23, the figure F24, and the figure F25 are located at the four corners of a rectangular frame FR1 surrounding the region of interest R6 such that the horizontal line segments and the vertical line segments are superimposed on the rectangular frame FR1.

Figure 19:
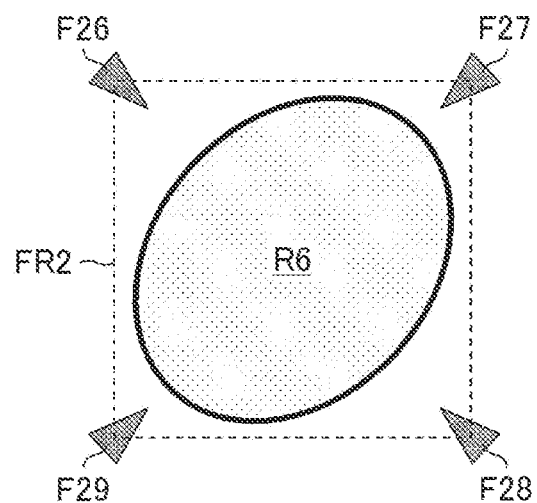
FIG. 19 is a diagram illustrating four figures surrounding a region of interest.

FIG. 19 is a diagram illustrating four figures which are a figure F26, a figure F27, a figure F28, and a figure F29 surrounding the region of interest R6. The figure F26, the figure F27, the figure F28, and the figure F29 are figures having the same isosceles triangle shape and having different orientations. The figure F26, the figure F27, the figure F28, and the figure F29 are located at the four corners of a rectangular frame FR2 surrounding the region of interest R6 such that the vertexes of the isosceles triangles are oriented toward the center of gravity of the region of interest R6.

Figure 20:
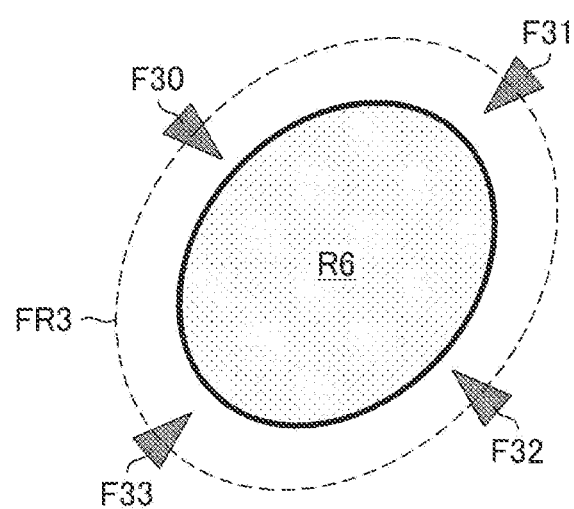
FIG. 20 is a diagram illustrating four figures surrounding a region of interest.

FIG. 20 is a diagram illustrating four figures which are a figure F30, a figure F31, a figure F32, and a figure F33 surrounding the region of interest R6. The figure F30, the figure F31, the figure F32, and the figure F33 are figures having the same isosceles triangle shape and having different orientations. The figure F30, the figure F31, the figure F32, and the figure F33 are located at individual positions on an oval frame FR3 surrounding the region of interest R6 such that the vertexes of the isosceles triangles are oriented toward the center of gravity of the region of interest R6.

As a result of superimposing the figures in this manner, even in a case where the region of interest is relatively small, it is possible to cause a user to recognize the region of interest.

Manner of Changing Number in Accordance with Size of Region of Interest

The number of figures superimposed on a region of interest is not necessarily fixed. For example, the figure generating unit 48 may change the number of figures to be generated by using, as a threshold value, a certain fixed fifth area of a region of interest.

Figure 21:
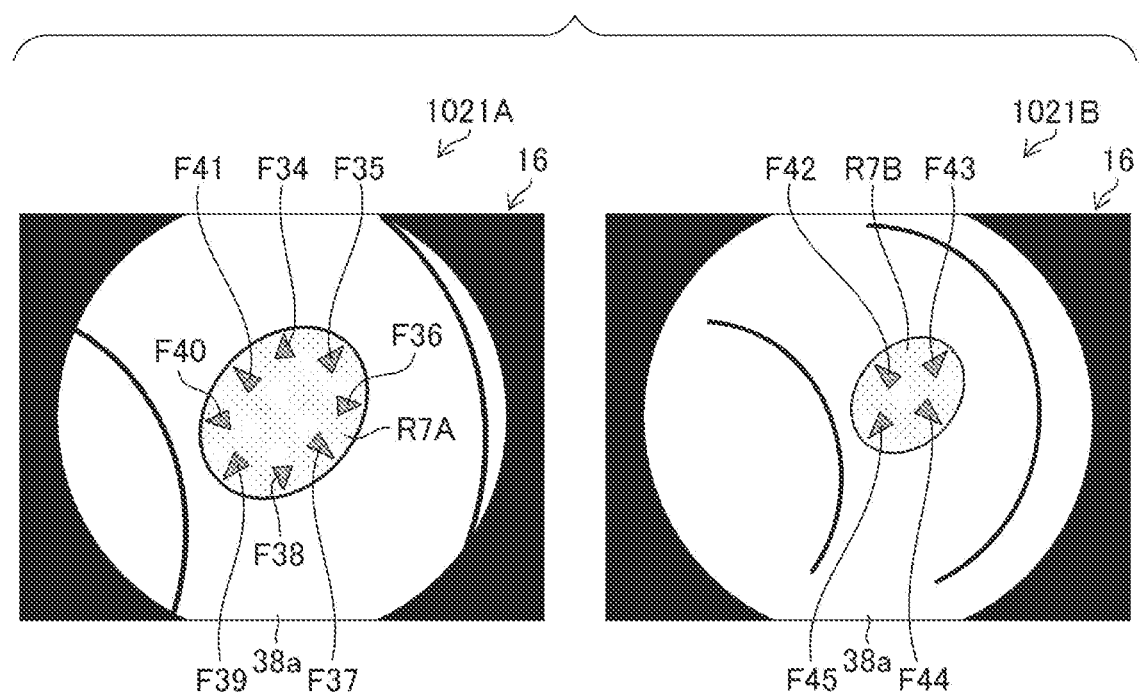
FIG. 21 is a diagram illustrating examples of display on the display.

FIG. 21 is a diagram illustrating examples of display on the display 16. In parts 1021A and 1021B illustrated in FIG. 21, the frame images 38a respectively including a region of interest R7A and a region of interest R7B are displayed. Here, the relationship "the area of the region of interest R7A>the fifth area>the area of the region of interest R7B" is satisfied.

As illustrated in FIG. 21, eight figures which are a figure F34, a figure F35, a figure F36, a figure F37, a figure F38, a figure F39, a figure F40, and a figure F41 are superimposed on the region of interest R7A whose area is larger than or equal to the fifth area. On the other hand, on the region of interest R7B whose area is smaller than the fifth area, four figures which are a figure F42, a figure F43, a figure F44, and a figure F45 are superimposed.

In this way, as a result of superimposing a larger number of figures as the area of the region of interest increases, it is possible to report the region of interest without hindering observation of the boundary between the region of interest and a region of non-interest in a medical image.

Others

The above-described medical image processing method can be configured as a program for causing a computer to implement individual steps, and it is possible to configure a non-transitory recording medium, such as a compact disc-read only memory (CD-ROM), storing the program.

A description has been given above of an example of superimposing a figure on an endoscopic image. A medical image on which a figure is superimposed is not limited to an endoscopic image, and may be an ultrasound image, a computed tomography (CT) image, a magnetic resonance imaging (MRI) image, or the like.

In the embodiment described above, the endoscope processor apparatus 12 and the medical image processing apparatus 14 have been described as apparatuses different from each other. Alternatively, the endoscope processor apparatus 12 and the medical image processing apparatus 14 may be integrated together as the endoscope processor apparatus 12 having the function of the medical image processing apparatus 14.

The hardware structure of a processing unit that executes various processes of the endoscope processor apparatus 12 and the medical image processing apparatus 14 includes various types of processors described below. The various types of processors include a central processing unit (CPU), which is a general-purpose processor that executes software (program) and functions as various processing units; a graphics processing unit (GPU), which is a processor specializing in image processing; a programmable logic device (PLD), which is a processor whose circuit configuration is changeable after manufacturing, such as a field programmable gate array (FPGA); a dedicated electric circuit, which is a processor having a circuit configuration designed exclusively for executing specific processing, such as an application specific integrated circuit (ASIC), and the like.

A single processing unit may be constituted by one of these various types of processors or may be constituted by two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of these various types of processors is, more specifically, electric circuitry including a combination of circuit elements, such as semiconductor elements.

The technical scope of the present invention is not limited to the scope described in the above embodiments. The components in the individual embodiments can be appropriately combined between embodiments without deviating from the gist of the present invention.

REFERENCE SIGNS LIST 9 endoscope system
10 endoscope
11 light source apparatus
12 endoscope processor apparatus
13 display apparatus
14 medical image processing apparatus
15 operation unit
16 display
20 insertion section
21 handheld operation section
22 universal cord
25 soft part
26 bending part
27 distal end part
28 imaging device
29 bending operation knob
30 air/water supply button
31 suction button
32 still image capturing instruction unit
33 treatment tool port
35 light guide
36 signal cable
37a connector
37b connector
38 moving image
38a frame image
39 still image
40 time-series image acquiring unit
42 region-of-interest detecting unit
44 coordinate calculating unit
46 area calculating unit
48 figure generating unit
50 control unit
52 display control unit
52A image display control unit
52B reporting information display control unit
54 storage unit
56 program
FR1 to FR3 frame
F1 to F45 figure
R1 to R7B region of interest
SQ1 rectangle
S1 to S6 individual steps of medical image processing method

What is claimed is:

1. A medical image processing apparatus comprising a processor configured to:
    calculate coordinates of a boundary between a region of interest in a medical image and a region of non-interest in the medical image, the region of interest being a region of a lesion portion, the region of non-interest being a region other than the region of interest; and
    superimpose, on the medical image, a figure pointing to the boundary in accordance with the calculated coordinates, on an inside of the region of interest such that at least part of the boundary is not superimposed with the figure.

2. The medical image processing apparatus according to claim 1, wherein the processor is further configured to:
    acquire the medical image; and
    acquire region-of-interest information from the medical image.

3. The medical image processing apparatus according to claim 1, wherein the processor is configured to superimpose a figure representing a center of gravity of the region of interest on the region of interest.

4. The medical image processing apparatus according to claim 1, wherein the processor is configured to superimpose the figure, the figure having a size corresponding to an area of the region of interest.

5. The medical image processing apparatus according to claim 4, wherein the processor is configured to superimpose the figure, the figure having a fixed first size, in a case where the area of the region of interest is larger than or equal to a first area.

6. The medical image processing apparatus according to claim 4, wherein the processor is configured to superimpose the figure, the figure having a fixed second size, in a case where the area of the region of interest is smaller than or equal to a second area.

7. The medical image processing apparatus according to claim 1, wherein the processor is configured to superimpose the figure, the figure having a shape corresponding to an area of the region of interest.

8. The medical image processing apparatus according to claim 7, wherein the processor is configured to superimpose a figure pointing to the boundary from the inside of the region of interest in a case where the area of the region of interest is larger than or equal to a third area, and superimpose a figure representing coordinates in the inside of the region of interest in a case where the area of the region of interest is smaller than the third area.

9. The medical image processing apparatus according to claim 7, wherein the processor is configured to superimpose the figure pointing to the boundary from the inside of the region of interest in a case where the area of the region of interest is larger than or equal to a fourth area, and superimpose the figure on an outside of the region of interest in a case where the area of the region of interest is smaller than the fourth area.

10. The medical image processing apparatus according to claim 1, wherein the processor is further configured to generate the figure.

11. The medical image processing apparatus according to claim 1, wherein the processor is further configured to cause a display to display the medical image on which the figure is superimposed.

12. A diagnosis support apparatus comprising:
the medical image processing apparatus according to claim 11; and
the display.

13. A medical image processing method comprising:
calculating coordinates of a boundary between a region of interest in a medical image and a region of non-interest in the medical image, the region of interest being a region of a lesion portion, the region of non-interest being a region other than the region of interest; and
superimposing, on the medical image, a figure pointing to the boundary in accordance with the calculated coordinates, on an inside of the region of interest such that at least part of the boundary is not superimposed with the figure.

14. A non-transitory computer-readable recording medium storing instructions that, when read by a computer, cause the computer to execute the medical image processing method according to claim 13.

* * * * *